United States Patent
Wagner

(10) Patent No.: US 6,957,104 B2
(45) Date of Patent: Oct. 18, 2005

(54) VENTRICULAR PACING FOR PREVENTION OF ATRIAL FIBRILLATION

(75) Inventor: Darrell Wagner, Isanti, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 354 days.

(21) Appl. No.: 10/038,498

(22) Filed: Jan. 3, 2002

(65) Prior Publication Data

US 2003/0125775 A1 Jul. 3, 2003

(51) Int. Cl.⁷ .............................................. A61N 1/362
(52) U.S. Cl. ........................................................ 607/9
(58) Field of Search ................................ 607/4, 5, 9, 14, 607/15, 25, 26

(56) References Cited

U.S. PATENT DOCUMENTS

| | | | |
|---|---|---|---|
| 4,363,325 A | * 12/1982 | Roline et al. .................... 607/9 |
| 4,412,541 A | 11/1983 | Schaldach et al. ............ 128/419 |
| 4,452,248 A | 6/1984 | Keller, Jr. ..................... 128/419 |
| 5,042,497 A | 8/1991 | Shapland ...................... 600/509 |
| 5,133,350 A | * 7/1992 | Duffin ............................ 607/6 |
| 5,247,930 A | 9/1993 | Begemann et al. ............. 607/11 |
| 5,340,361 A | 8/1994 | Sholder ......................... 607/24 |
| 5,403,356 A | 4/1995 | Hill et al. ...................... 607/14 |
| 5,514,161 A | 5/1996 | Limousin ........................ 607/9 |
| 5,674,251 A | 10/1997 | Combs et al. ................... 607/4 |
| 5,683,429 A | * 11/1997 | Mehra ........................... 607/14 |
| 5,713,929 A | 2/1998 | Hess et al. ..................... 607/14 |
| 5,716,383 A | * 2/1998 | Kieval et al. .................... 607/9 |
| 5,782,887 A | * 7/1998 | van Krieken et al. .......... 607/25 |
| 5,978,709 A | 11/1999 | Begemann et al. ............. 607/14 |
| 6,122,545 A | * 9/2000 | Struble et al. ................... 607/9 |
| 6,292,694 B1 | 9/2001 | Schloss et al. ................... 607/9 |
| 6,330,477 B1 | * 12/2001 | Casavant ....................... 607/14 |
| 6,377,852 B1 | * 4/2002 | Bornzin et al. ................... 607/9 |
| 6,408,210 B1 | * 6/2002 | Bornzin et al. ................ 607/28 |
| 6,522,922 B1 | * 2/2003 | Perschbacher et al. ........ 607/14 |
| 6,553,258 B2 | * 4/2003 | Stahmann et al. ............... 607/9 |
| 2002/0062139 A1 | * 5/2002 | Ding ............................. 607/25 |

* cited by examiner

*Primary Examiner*—Jeffrey R. Jastrzab
(74) *Attorney, Agent, or Firm*—Schwegman, Lundberg, Woessner & Kluth, P.A.

(57) ABSTRACT

A method and apparatus for preventing atrial fibrillation arising from a premature atrial contraction. Upon detection of a premature atrial contraction, a pace is delivered to a ventricle at a specified AV interval selected as either a late-pace or early-pace value. The resulting ventricular depolarization then occurs during a time when the atria are not vulnerable to the triggering of fibrillation.

14 Claims, 2 Drawing Sheets

VENTRICULAR PACING FOR PREVENTION OF ATRIAL FIBRILLATION

FIELD OF THE INVENTION

This invention pertains to systems and methods for cardiac rhythm management. In particular, the invention relates to cardiac pacemakers and their methods of operation.

BACKGROUND

Tachyarrhythmias are abnormal heart rhythms characterized by a rapid heart rate, typically expressed in units of beats per minute (bpm). They can occur in either chamber of the heart (i.e., ventricles or atria) or both. Examples of tachyarrhythmias include sinus tachycardia, ventricular tachycardia, ventricular fibrillation (VF), atrial tachycardia, and atrial fibrillation (AF). Tachycardia is characterized by a rapid rate, either due to an ectopic excitatory focus or abnormal excitation by normal pacemaker tissue, while fibrillation occurs when the chamber depolarizes in a chaotic fashion with abnormal depolarization waveforms as reflected by an EKG.

An electrical shock applied to a heart chamber (i.e., defibrillation or cardioversion) can be used to terminate most tachyarrhythmias by depolarizing excitable myocardium, which thereby prolongs refractoriness, interrupts reentrant circuits, and discharges excitatory foci. Implantable cardioverter/defibrillators (ICDs) provide this kind of therapy by delivering a shock pulse to the heart when fibrillation is detected by the device. ICDs can be designed to treat either atrial or ventricular tachyarrhythmias, or both, and may also incorporate cardiac pacing functionality. The most dangerous tachyarrhythmias are ventricular tachycardia and ventricular fibrillation, and ICDs have most commonly been applied in the treatment of those conditions.

ICDs are also capable, however, of detecting atrial tachyarrhythmias, such as atrial fibrillation and atrial flutter, and delivering a shock pulse to the atria in order to terminate the arrhythmia. Although not immediately life threatening, it is important to treat atrial fibrillation for several reasons. First, atrial fibrillation is associated with a loss of atrioventricular synchrony which can be hemodynamically compromising and cause such symptoms as dyspnea, fatigue, vertigo, and angina. Atrial fibrillation can also predispose to strokes resulting from emboli forming in the left atrium. Although drug therapy and/or in-hospital cardioversion are acceptable treatment modalities for atrial fibrillation, ICDs configured to treat atrial fibrillation offer a number of advantages to certain patients, including convenience and greater efficacy. It would be even more beneficial if an implantable device could deliver electro-stimulatory therapy in a manner that would prevent the occurrence of atrial fibrillation.

SUMMARY OF THE INVENTION

Certain episodes of atrial fibrillation may be caused by the ventricular depolarization following a premature atrial contraction. The ventricular depolarization in this situation stimulates the atrium during its vulnerable period, thus triggering the arrhythmia. This type of atrial fibrillation can be prevented by pacing the ventricles at an instant following a premature atrial contraction that is either before or after the atrial vulnerable period. Such ventricular pacing therapy for prevention of atrial fibrillation may be implemented in a patient either alone or in conjunction with other pacing therapy.

This description is intended to provide an overview of the subject matter of the present patent application and is not an exhaustive or exclusive explanation of the invention.

DETAILED DESCRIPTION

Figure 1:
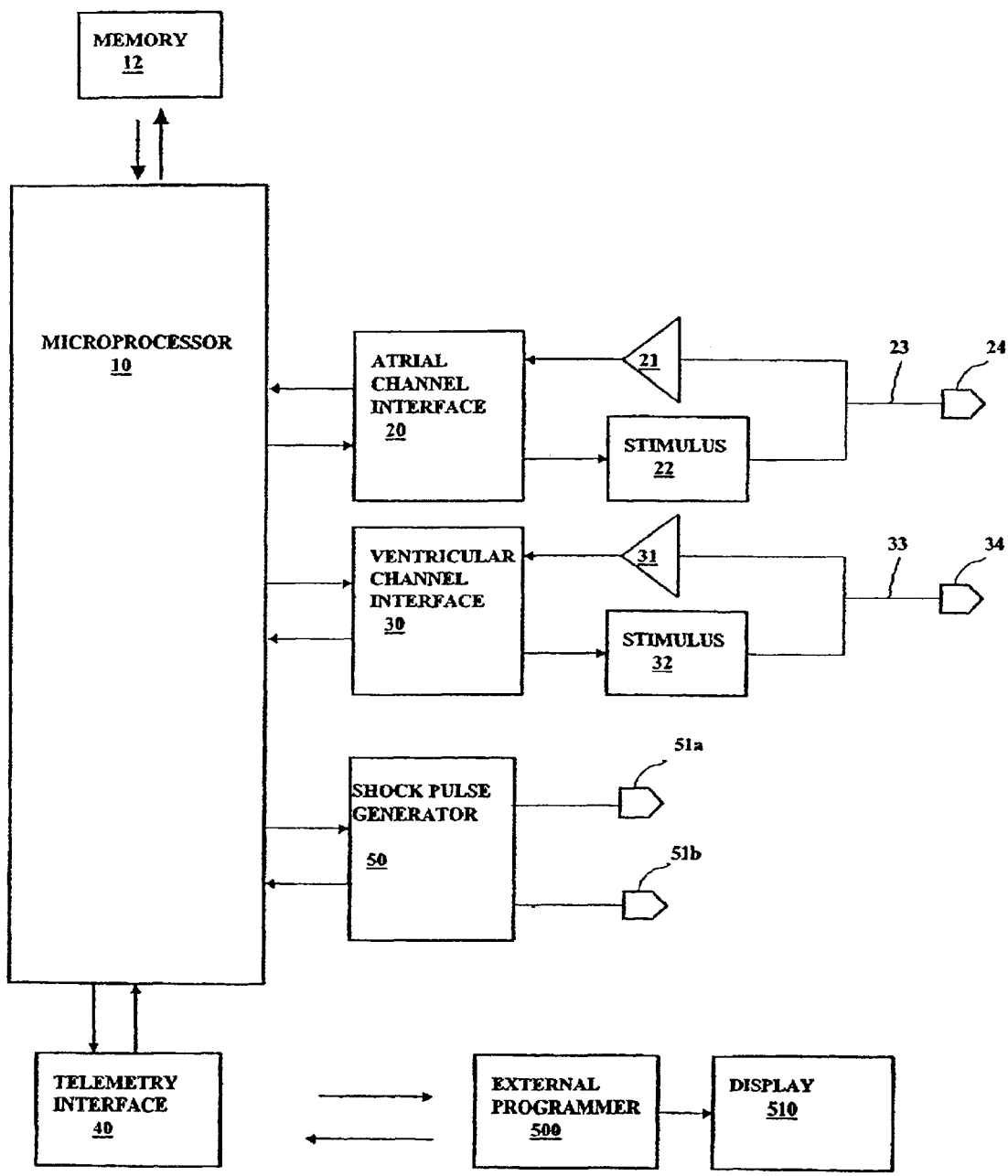
FIG. 1 is a system diagram of a pacemaker.

Premature atrial contractions (PACs) are atrial contractions resulting from ectopic excitatory foci in the atria that occur prior to the time they would normally be expected. Such premature excitation of the atria spreads to the atrioventricular (AV) node and may or may not be conducted to the ventricles depending upon whether the AV node is still refractory from the preceding beat. Ectopic foci can be due to local areas of ischemia, but premature atrial contractions can also occur in normal persons when provoked by drugs, alcohol, caffeine, or tobacco.

The atria are normally activated by an excitatory impulse originating in the SA node which then spreads throughout the atria and to the AV node, where it is then conducted by the His bundles and Purkinje fibers to activate the ventricles. When a PAC occurs, the excitation spreads from the ectopic site to the AV node so that the ectopic site in the atrium is depolarized sooner relative to the time of the subsequent ventricular depolarization than is normally the case. This means that the atrial ectopic site also repolarizes sooner as well, so that its vulnerable period may coincide with the ventricular depolarization. If the ventricular depolarization is conducted retrogradely back to the atria during the vulnerable period, atrial fibrillation may be triggered. The mechanical stresses induced in the atria by ventricular contraction may also be responsible for triggering atrial fibrillation.

Ventricular pacing may be employed to prevent the type of atrial fibrillation described above by pacing the ventricles while the atria are not in a vulnerable period after a PAC is detected. One way of detecting PACs is to measure the interval between successive atrial senses, referred to as the A—A interval, and declare an atrial sense to be a PAC if the current A—A interval is less than a specified percentage of the preceding A—A interval or some average of preceding A—A intervals. Upon detection of a PAC, a ventricular pace may then be delivered at an AV delay interval shorter than the intrinsic AV conduction time so that the ventricular depolarization occurs earlier with respect to the PAC than would naturally occur and before the most vulnerable period of the atrium. The timing of the ventricular pace may also be constrained by a minimum interval from the previous ventricular sense or pace so as to avoid pacing the ventricle during its vulnerable period.

If a patient suffers from an AV block so that either the intrinsic AV conduction time is abnormally long or no AV conduction pathway exists, a different method of ventricular pacing after a PAC may be used. Patients with an AV block may be treated with an implantable pacemaker operating in a bradycardia pacing mode. In a DDD or VDD mode, for example, a ventricular pace is triggered after a programmed AV delay interval following an atrial sense to thus simulate an intact AV conduction pathway. The programmed AV interval is normally set at a value that produces optimum hemodynamic performance. When a PAC occurs, however, and if a ventricular pace is delivered at the normal programmed AV interval, the ventricles may depolarize during the atrial vulnerable period. The pacemaker may therefore be configured to undergo a mode switch upon detection of a PAC that lengthens the programmed AV delay interval. The ventricular pace is then delayed so that the ventricular depolarization occurs after the most vulnerable period of the atrium.

Described below is an exemplary device for carrying out ventricular pacing in order to prevent the triggering of atrial fibrillation by a PAC. Such pacing may be the sole pacing therapy given to the patient, or it may be delivered in combination with a bradycardia pacing mode.

1. Hardware Platform

Cardiac rhythm management devices are implantable devices that provide electrical stimulation to selected chambers of the heart in order to treat disorders of cardiac rhythm and include pacemakers and implantable cardioverter/defibrillators. A pacemaker is a cardiac rhythm management device that paces the heart with timed pacing pulses. The term "pacemaker" as used herein should be taken to mean any device with a pacing functionality, such as an implantable cardioverter/defibrillator with a pacemaker incorporated therein.

In the description that follows, a microprocessor-based cardiac rhythm management device will be referred to as incorporating the system and method that is the present invention. In the embodiment to be described, the invention is implemented with a control unit made up of a microprocessor executing programmed instructions in memory. It should be appreciated, however, that certain functions of a cardiac rhythm management device could be controlled by custom logic circuitry either in addition to or instead of a programmed microprocessor. The terms "controller" or "circuitry" as used herein should therefore be taken to encompass either custom circuitry (i.e., dedicated hardware) or a microprocessor executing programmed instructions contained in a processor-readable storage medium along with associated circuit elements.

Implantable cardiac rhythm management devices, such as pacemakers and ICD's, are electronic devices that are implanted subcutaneously on a patient's chest with leads threaded intravenously into the heart to connect the device to electrodes used for sensing electrical activity and for electrical stimulation of the heart. FIG. 1 is a system diagram of a microprocessor-based cardiac rhythm management device with the capability of delivering cardioversion/defibrillation shocks as well as antitachycardia pacing (ATP) therapy. The device may also be configured to deliver conventional (e.g., bradycardia) pacing as well. The controller 10 of the pacemaker is a microprocessor that communicates with a memory 12 via a bidirectional data bus. The memory 12 typically comprises a ROM (read-only memory) for program storage and a RAM (random-access memory) for data storage. The pacemaker has atrial and ventricular sensing/pacing channels that respectively include electrodes 24 and 34, leads 23 and 33, sensing amplifiers 21 and 31, pulse generators 22 and 32, and channel interfaces 20 and 30. Incorporated into each sensing/pacing channel is thus a pacing channel made up of the pulse generator connected to the electrode and a sensing channel made up of the sense amplifier connected to the electrode. In this embodiment, a single electrode is used for sensing and pacing in each channel, known as a unipolar lead. Other embodiments may employ bipolar leads that include two electrodes for outputting a pacing pulse and/or sensing intrinsic activity. The channel interfaces communicate bidirectionally with microprocessor 10 and include analog-to-digital converters for digitizing sensing signal inputs from the sense amplifiers and registers that can be written to by the microprocessor in order to adjust the gain and threshold values for the sensing amplifiers, output pacing pulses, and change the pacing pulse amplitude and/or duration. A telemetry interface 40 is also provided for communicating with an external programmer 500 that has an associated display 510.

The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. The sensing circuitry of the pacemaker detects a chamber sense when an electrogram signal (i.e., a voltage sensed by an electrode representing cardiac electrical activity) generated by a particular channel exceeds a specified detection threshold. A chamber sense may be either an atrial sense or a ventricular sense depending on whether it occurs in the atrial or ventricular sensing channel. Pacing algorithms used in particular pacing modes employ such senses to trigger or inhibit pacing. By measuring the interval between successive atrial senses, the controller is also able to detect PACs such as by the method described above.

2. Bradycardia Pacing Modes

The most common condition for which pacemakers are used is the treatment of bradycardia where the intrinsic heart rate is too slow. The two most common causes of ventricular bradycardia are AV block and sick sinus syndrome. Permanent pacing for bradycardia is indicated in patients with symptomatic bradycardia of any type as long as it is likely to be permanent or recurrent and is not associated with a transient condition from which the patient may recover. Bradycardia pacing modes refer to pacing algorithms used to pace the atria and/or ventricles when the intrinsic atrial and/or ventricular rate is inadequate due to, for example, AV conduction blocks or sinus node dysfunction. Such modes may either be single-chamber pacing, where either an atrium or a ventricle is paced, or dual-chamber pacing in which both an atrium and a ventricle are paced. The modes are generally designated by a letter code of three positions where each letter in the code refers to a specific function of the pacemaker. The first letter refers to which heart chambers are paced and which may be an A (for atrium), a V (for ventricle), D (for both chambers), or O (for none). The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used), and O (for no response). Modern pacemakers are typically programmable so that they can operate in any mode which the physical configuration of the device will allow. Additional sensing of physiological data allows some pacemakers to change the rate at which they pace the heart in accordance with some parameter correlated to metabolic demand. Such pacemakers are called rate-adaptive pacemakers and are designated by a fourth letter added to the three-letter code, R.

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In atrial tracking pacemakers (i.e., VDD or DDD mode), another ventricular escape interval is defined between atrial and ventricular events, referred to as the atrio-ventricular interval (or AV interval). The atrio-ventricular interval is triggered by an atrial sense or pace and stopped by a ventricular sense or pace. A ventricular pace is delivered upon expiration of the atrio-ventricular interval if no ventricular sense occurs before. Atrial-tracking ventricular pacing attempts to maintain the atrio-ventricular synchrony occurring with physiological beats whereby atrial contractions augment diastolic filling of the ventricles. In chronotropically competent patients (i.e., those patients whose atrial rhythm is responsive to metabolic demand) in need of ventricular pacing, atrial triggered modes such as DDD or VDD are desirable because they allow the pacing to track the physiologically normal atrial rhythm, which causes cardiac output to be responsive to the metabolic needs of the body.

A pacemaker can also be configured to pace the atria on an inhibited demand basis. An atrial escape interval is then defined as the maximum time interval in which an atrial sense must be detected after a ventricular sense or pace before an atrial pace will be delivered. When atrial inhibited demand pacing is combined with atrial-triggered ventricular demand pacing (i.e., DDD mode), both the atria and ventricles are paced in the absence of intrinsic activity, termed AV sequential pacing. The lower rate limit interval is then the sum of the atrial escape interval and the atrio-ventricular interval.

Cardiac resynchronization therapy is pacing stimulation applied to one or more heart chambers in a manner that restores or maintains synchronized contractions of the atria and/or ventricles and thereby improves pumping efficiency. One way to deliver resynchronization therapy is to pace a site with a synchronous bradycardia pacing mode and then deliver one or more resynchronization paces to one or more additional pacing sites in a defined time relation to one or more selected sensing or pacing events that either reset escape intervals or trigger paces in the bradycardia pacing mode.

Ventricular pacing after PAC detection in order to prevent atrial fibrillation may be implemented in conjunction with any of the bradycardia pacing modes discussed above. As described below, however, the implementation may be slightly different depending upon whether the mode is an atrial tracking or non-atrial tracking mode.

3. AF Prevention Combined with Non-Atrial Tracking Bradycardia Mode

Figure 2A:
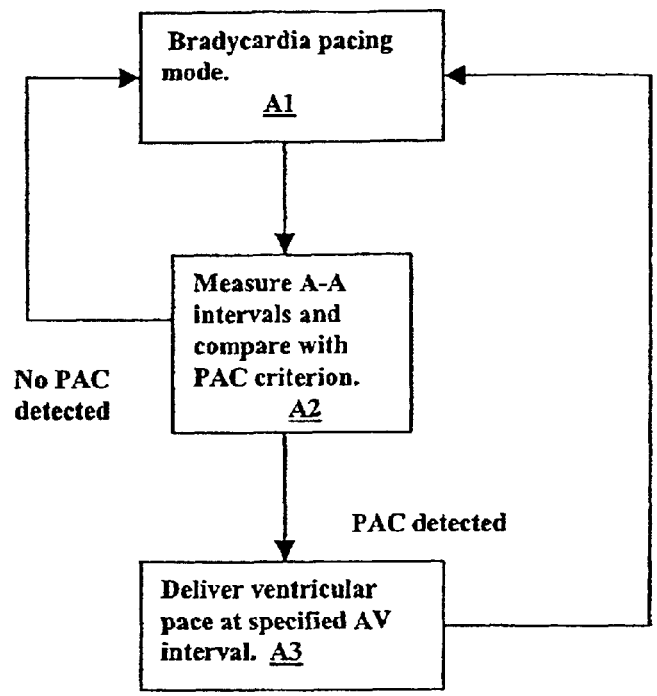
FIGS. 2A and 2B illustrate the steps involved in exemplary implementations.

FIG. 2A illustrates an exemplary scheme by which the device in FIG. 1 may be configured to deliver ventricular pacing for preventing atrial fibrillation either when no other pacing therapy is being delivered or in combination with a non-atrial tracking bradycardia pacing mode. Step A1 represents the normal bradycardia pacing mode that the device uses to deliver pacing when no PAC has been detected. At step A2, the device measures successive A—A intervals and compares each such interval with the criteria for declaring a PAC. If no PAC is detected, the device returns to the bradycardia pacing mode at step A1 or, in the case where no bradycardia pacing is being delivered, returns to monitoring A—A intervals at step A2. When a PAC is detected, the device delivers a ventricular pace at step A3 at a specified AV interval selected to be either: 1) an early-pace AV interval that is less than the intrinsic AV conduction time and results in a ventricular pace before the atrium's vulnerable period, or 2) a late-pace AV interval that results in a ventricular pace after the atrium's vulnerable period. The value of the early-pace AV interval may be specified by the clinician and set using an external programmer, or may be set automatically by the device as a percentage of the intrinsic AV conduction time measured from electrogram signals during an intrinsic heartbeat. When the early-pace AV interval is used, the device may constrain the AV interval so that the ventricular pace is delivered after a specified minimum interval from the previous ventricular sense or pace in order to avoid pacing the ventricle during its vulnerable period. The late-pace AV interval can be used when the patent has a complete AV block so that no physiological conduction from the atria to the ventricles occurs. The late-pace AV interval results in the ventricular pace being delivered after the vulnerable period of the atrium has passed. The value of the late-pace AV interval can be determined by a clinician from electrophysiological measurements and set using an external programmer. After the ventricular pace is delivered, the device returns to the bradycardia pacing mode at step A1 and/or monitoring A—A intervals at step A2.

4. AF Prevention Combined with Atrial Tracking Bradycardia Mode

Figure 2B:
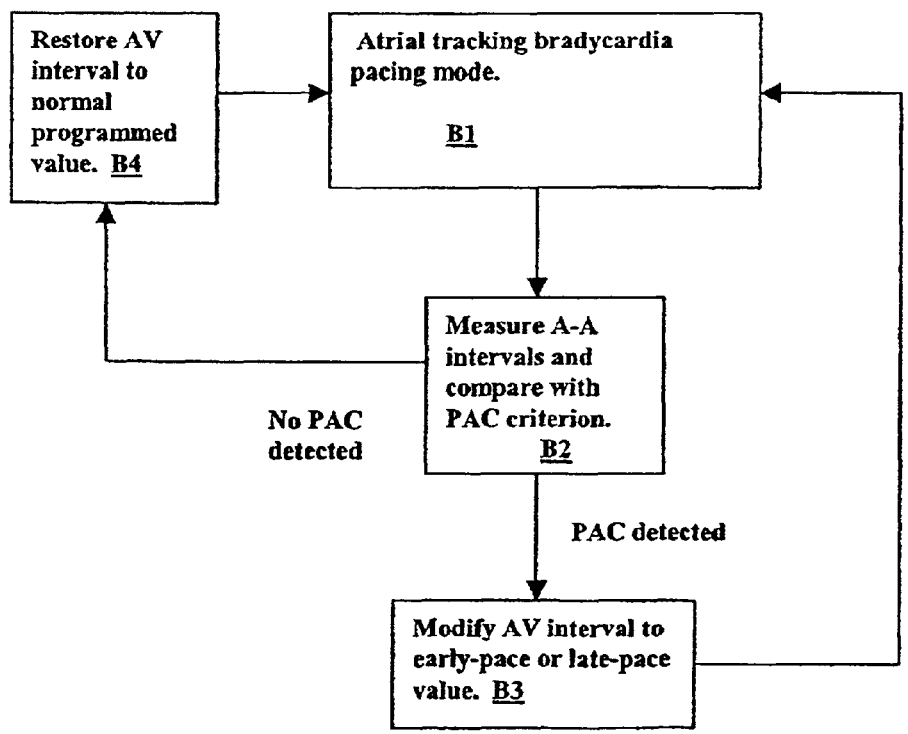

FIG. 2B illustrates an alternative scheme for delivering ventricular pacing to prevent atrial fibrillation in conjunction with an atrial tracking bradycardia pacing mode (i.e., either DDD or VDD). As described above, such a mode normally employs a programmed AV interval to deliver a ventricular pace after an atrial sense. Ventricular pacing after a PAC is detected can thus be implemented as a mode switch in which the AV interval is modified to be either a late-pace AV interval or an early-pace AV as described above. Step B1 represents the normal bradycardia pacing mode with atrial tracking, which may also include AV sequential pacing (i.e., DDD mode). At step B2, successive A—A intervals are measured and compared with the criteria for declaring a PAC. If a PAC is detected, the AV interval is adjusted at step B3 to either a late-pace AV interval or an early-pace AV interval as described above. The device then returns to the bradycardia mode at step B1 which carries out the ventricular pacing using the adjusted AV interval. The next A—A interval is then measured and, if no PAC is detected, the AV interval is set to its normal programmed value at step B4, and bradycardia pacing is resumed at step B1.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac rhythm management device, comprising:
   an atrial sensing channel for generating atrial electrogram signals;
   circuitry for detecting atrial senses when the atrial electrogram signal exceeds a specified threshold;
   circuitry for measuring a time interval between successive atrial senses and for detecting a premature atrial contraction when the time interval meets a specified criterion;
   a ventricular pacing channel for delivering pacing pulses to a ventricle; and,
   circuitry for causing a ventricular pace to be delivered only when a premature atrial contraction is detected, wherein the ventricular pace is delivered at a specified AV interval following the premature atrial contraction.

2. The device of claim 1 wherein the specified AV interval is a late-pace value.

3. The device of claim 1 wherein the specified AV interval is an early-pace value.

4. The device of claim 3 wherein the AV interval is constrained so that the ventricular pace is delivered after a specified minimum interval from the previous ventricular sense or ventricular pace.

5. A cardiac rhythm management device, comprising:
   an atrial sensing channel for generating atrial electrogram signals;
   circuitry for detecting atrial senses when the atrial electrogram signal exceeds a specified threshold;
   circuitry for measuring a time interval between successive atrial senses and for detecting a premature atrial contraction when the time interval meets a specified criterion;
   a ventricular pacing channel for delivering pacing pulses to a ventricle;
   circuitry for causing a ventricular pace to be delivered in accordance with an atrial tracking bradycardia pacing mode such that a ventricular pace is delivered at a specified AV interval following an atrial sense;
   circuitry for shortening the AV interval to an early-pace value when a premature atrial contraction is detected.

6. The device of claim 5 wherein the AV interval is constrained so that the ventricular pace is delivered after a specified minimum interval from the previous sensed or paced ventricular beat.

7. The device of claim 5 wherein the bradycardia pacing mode includes AV sequential pacing.

8. A method for operating a cardiac rhythm management device, comprising:
   detecting an atrial sense when an atrial electrogram signal exceeds a specified threshold;
   measuring a time interval between successive atrial senses and detecting a premature atrial contraction when the time interval meets a specified criterion;
   delivering a pacing pulse to a ventricle only when a premature atrial contraction is detected, wherein the ventricular pace is delivered at a specified AV interval following the premature atrial contraction.

9. The method of claim 8 wherein the specified AV interval is a late-pace value.

10. The method of claim 8 wherein the specified AV interval is an early-pace value.

11. The method of claim 10 wherein the AV interval is constrained so that the ventricular pace is delivered after a specified minimum interval from the previous ventricular sense or ventricular pace.

12. A method for operating a cardiac rhythm management device, comprising:
    detecting an atrial sense when an atrial electrogram signal exceeds a specified threshold;
    measuring a time interval between successive atrial senses and detecting a premature atrial contraction when the time interval meets a specified criterion;
    delivering pacing pulses to a ventricle in accordance with an atrial tracking bradycardia pacing mode such that a ventricular pace is delivered at a specified AV interval following an atrial sense; and,
    shortening the AV interval to an early-pace value when a premature atrial contraction is detected.

13. The method of claim 12 wherein the AV interval is constrained so that the ventricular pace is delivered after a specified minimum interval from the previous sensed or paced ventricular beat.

14. The method of claim 12 wherein the bradycardia pacing mode includes AV sequential pacing.

* * * * *